United States Patent [19]

Segui Pastor et al.

[11] Patent Number: 5,019,043

[45] Date of Patent: May 28, 1991

[54] SYRINGE WITH NEEDLE RETRACTION CAPABILITY

[75] Inventors: Vicente M. Segui Pastor, Cuenca, 85, E-46008 Valencia; Amando Galiana Sabater; Enrique Segui Pastor, both of Valencia, all of Spain

[73] Assignee: Vincent Miguel Segui Pastor, Valencia, Spain

[21] Appl. No.: 385,373

[22] Filed: Jul. 27, 1989

[30] Foreign Application Priority Data

Aug. 5, 1988 [ES] Spain .................................. 8802473

[51] Int. Cl.⁵ ............................................ A61M 5/00
[52] U.S. Cl. .................................. 604/110; 604/195
[58] Field of Search ............... 604/110, 193, 195, 197, 604/198, 240, 218

[56] References Cited

U.S. PATENT DOCUMENTS

| | | |
|---|---|---|
| 2,880,725 | 4/1959 | Kendall . |
| 2,888,923 | 6/1959 | Reis . |
| 2,935,067 | 4/1950 | Bouet . |
| 3,584,626 | 6/1971 | Johansson . |
| 4,026,287 | 5/1977 | Haller ................... 604/110 |
| 4,507,117 | 3/1985 | Vining et al. . |
| 4,631,057 | 12/1986 | Mitchell . |
| 4,639,249 | 1/1987 | Larson . |
| 4,643,199 | 1/1987 | Jennings, Jr. et al. . |
| 4,650,468 | 3/1987 | Jennings, Jr. . |
| 4,675,005 | 6/1987 | DeLuccia . |
| 4,692,156 | 9/1987 | Haller . |
| 4,710,170 | 12/1987 | Haber et al. . |
| 4,737,144 | 4/1988 | Choksi .................. 604/198 |
| 4,747,830 | 5/1988 | Gloyer et al. ........... 604/198 |
| 4,767,413 | 8/1988 | Haber et al. . |
| 4,770,655 | 9/1988 | Haber et al. ........... 604/110 |
| 4,813,936 | 3/1989 | Schroeder .............. 604/195 |
| 4,883,466 | 11/1989 | Glazier ................. 604/110 |
| 4,919,652 | 4/1990 | Alter et al. ........... 604/110 |
| 4,921,486 | 5/1990 | DeChellis et al. ...... 604/110 |

FOREIGN PATENT DOCUMENTS

| | | | |
|---|---|---|---|
| 0034231 | 2/1980 | European Pat. Off. . | |
| 0276160 | 1/1988 | European Pat. Off. . | |
| 0326983 | 8/1989 | European Pat. Off. | ............ 604/110 |
| 8904681 | 6/1989 | World Int. Prop. O. | .......... 604/110 |

*Primary Examiner*—Stephen C. Pellegrino
*Assistant Examiner*—Michael Rafa
*Attorney, Agent, or Firm*—Beveridge, DeGrandi & Weilacher

[57] ABSTRACT

A syringe with a plunger having a compressible piston at its forward end and a harpoon-shaped member extending forward and away from the piston. The plunger travels within a syringe casing which has locking openings at its rearward end. The harpoon-shaped members has a rearward member which biases two locking lugs outward. The harpoon-shaped member is releasably retained within a cavity in the piston. The plunger includes a pair of channels running along its length as well as a crosspiece positioned within each channel which provides a slot into which the locking lugs are received. Following an injection with the syringe, the piston and harpoon-shaped member are pushed forward into the casing resulting in a compression of the piston and the attachment of the harpoon-shaped member to an inner part of a needle holder. The plunger with attached needle can then be retracted until the two locking lugs snap into the openings formed in the outer casing. With the locking lugs received within the casing openings, it is possible to force the plunger forward resulting in the crosspieces snapping off and the disengagement of the piston from the harpoon-shaped member such that the plunger can be nestled within the syringe casing. In an alternate embodiment, a compressed spring forces the harpoon-shaped member rearwardly and into a locking arrangement with the casing openings following a shearing off of the crosspieces.

20 Claims, 4 Drawing Sheets

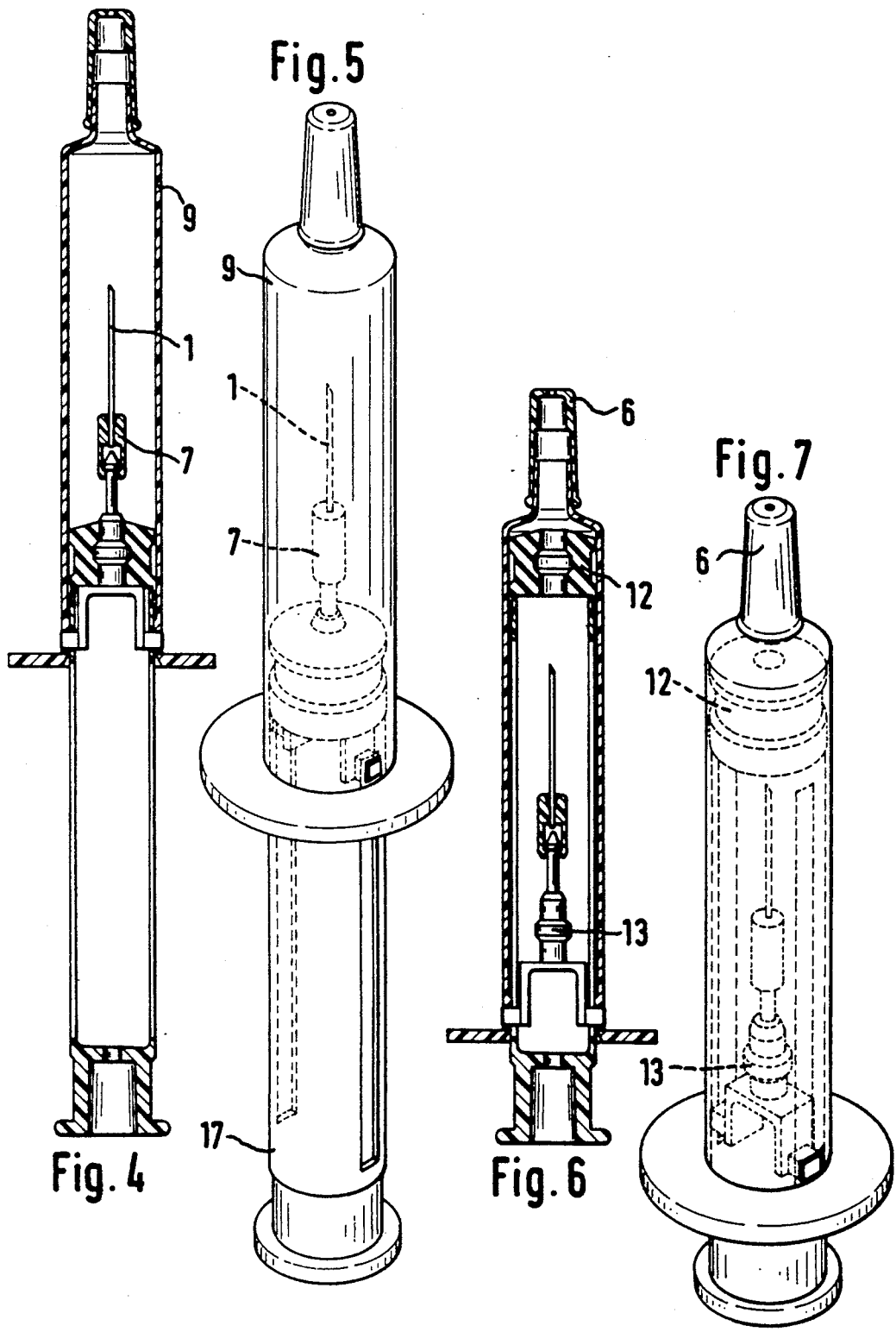

SYRINGE WITH NEEDLE RETRACTION CAPABILITY

FIELD OF THE INVENTION

The present invention consists of a new syringe with facilities for the optional retraction of the needle inside the cylinder after use. The purpose, clearly, is to avoid accidents which might transmit certain illnesses by contagion.

SUMMARY OF THE INVENTION

The present invention includes an outer cylinder within which a plunger with piston end fulfills the normal functions of a syringe but with the difference that the plunger is fitted with a small harpoon-shaped member having a cone or similar shaped tip at its end which, with the application of a certain amount of pressure, can lock into the inner part of the needle holder so that when the plunger is drawn back again the needle retracts and is swallowed up and is prevented from being taken out again by a restraining mechanism.

BRIEF DESCRIPTION OF THE DRAWINGS

In order to make the explanation that follows clearer and more intelligible, we attach to this report, as part of the same, four pages of drawings with eleven figures with represent, by way of example, the essence of the present invention. The eleven Figures includes the following.

FIG. 4 shows a cross-sectional view of the present invention with the plunger and needle retracted;

FIG. 5 shows a perspective view of that which is shown in FIG. 4;

FIG. 6 shows a cross-sectional view of the present invention with the needle fixed in its retracted position and the plunger extending to the forward end of the casing;

FIG. 7 shows a perspective view of that which is shown in FIG. 6.

FIG. 1 shows a cross-section of the syringe with the needle (1), its holder (2) and the plunger (4) which contains the needle situated in the recess (5) and the rim (3) which facilitates the pushing of the plunger.

BRIEF DESCRIPTION OF THE PREFERRED EMBODIMENT

Figure 9:
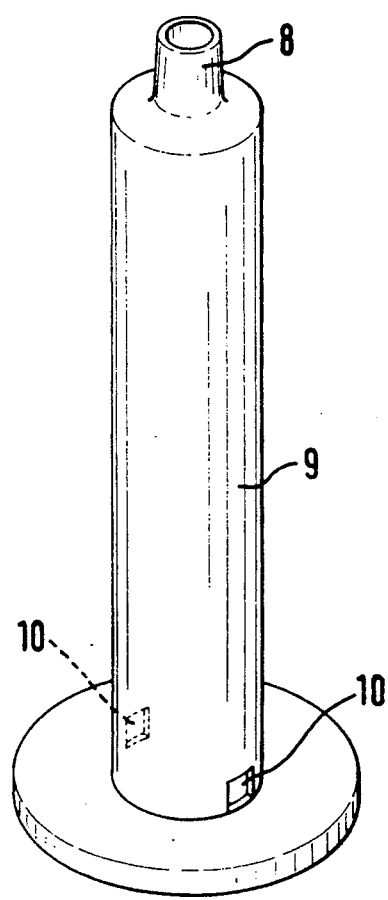
FIG. 9 shows a perspective view of the syringe casing.

In FIG. 9, the syringe casing (9) has openings (10) at the end, into which the plunger fin-shaped lugs (14) lock when the plunger detaches the needle from its holder by means of the plunger element (11) which is in the form of a harpoon shaped member with tip. The channels (16) on the side part of the plunger body facilitate the guiding of the fin-shaped lugs (14).

Figure 10:
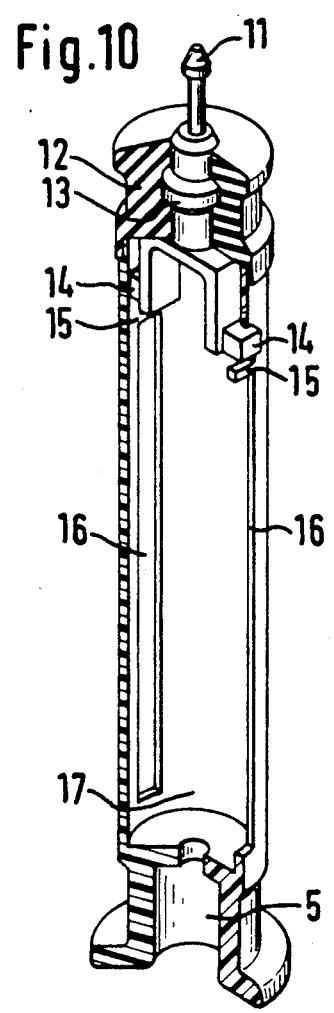
FIG. 10 shows a cut away view of the plunger.

In FIG. 10, we can see the plunger which consists of a piston (12) with a central core (13) connected to the harpoon-shaped member (11) which has already been mentioned and an "Ω"—shaped part which is under slight tension so that when the needle is extracted its lugs lock into the openings (10) in the body of the syringe casing (a). For this purpose, when the needle is extracted and the locking lugs (14) are received within openings (1) in casing (9) the plunger can again be moved forward into casing (9) following the breaking of crosspieces (15) by application of a sufficient force forward on the plunger. The breaking of crosspieces (15) thus allows for the downward or forward movement of the piston (12) already detached from the locking lugs (14) and the bulbous ring forming part of central core (13) and the maintenance of needle (1) in the area indicated as (17) in FIG. (10).

Figure 8:
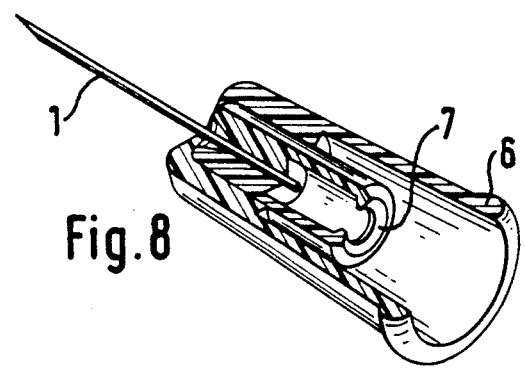
FIG. 8 shows a cut away view of the needle and the inner and outer needle parts.

This syringe is used in the usual familiar way. The needle is located in a separate casing as indicated in FIG. 8, stored at the rear of the plunger (5), and is fitted to the end of the syringe (8) solely to perform an injection, after which it can be extracted. The needle is secured to inner part (7) at one end and inner part (7) is positioned within outer part (6). Needle 1, inner part (7) and outer part (6) together form a needle assembly. The extraction of the needle results from the fact that it consists of two elements shown in FIG. 8 as (6) and (7), (6) being the outer part and (7) the inner part which is attached to the needle (1). To receive the cone shaped tip of harpoon shaped member 11, inner part 6 is formed of an elastic material or with a plurality of longitudinal channels.

The way in which the needle is extracted can be seen clearly illustrated in FIGS. 2-3, 4-5 and 6-7.

Figure 1:
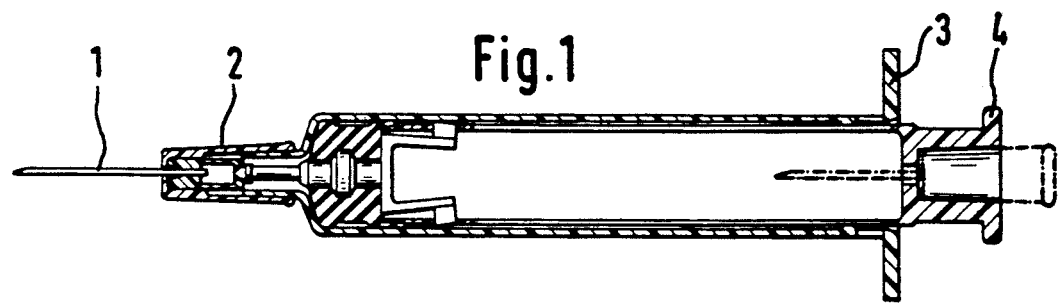
FIG. 1 shows a cross-sectional view of one embodiment of the present invention with the plunger positioned within the syringe casing and the harpoon shaped member free from attachment with the inner part of the needle holder.
Figures 2, 3:
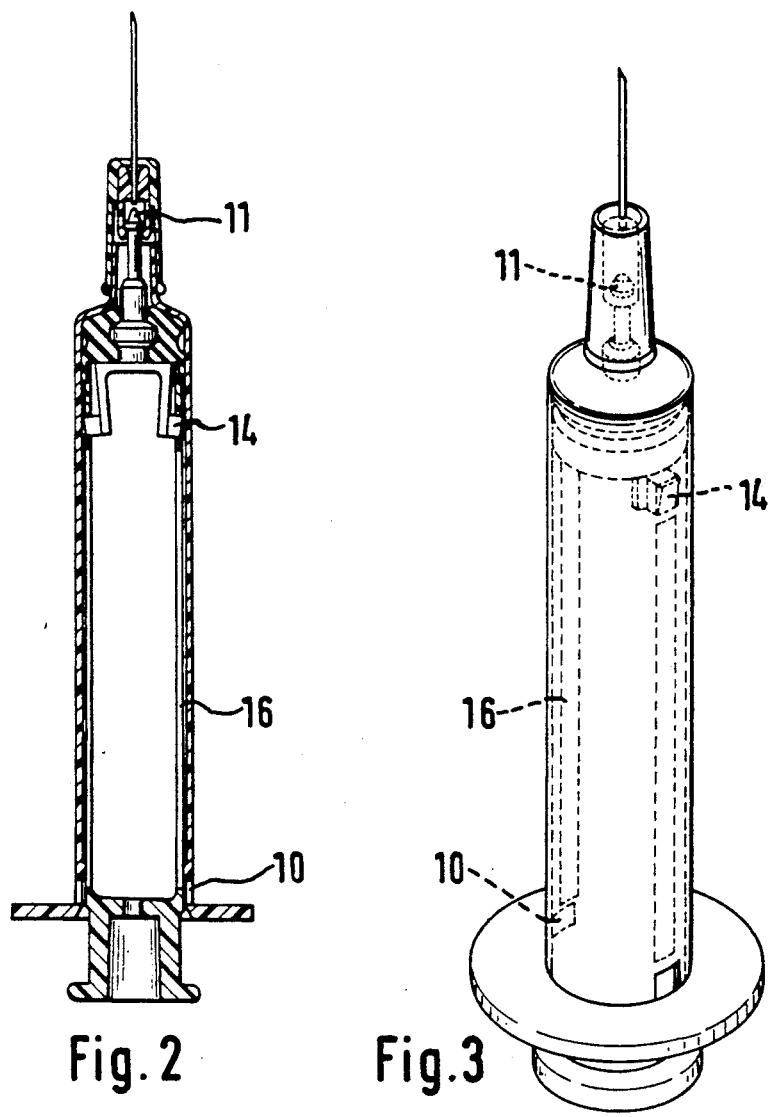
FIG. 2 shows a cross-sectional view of the embodiment of FIG. 1 with the harpoon shaped member attached to the inner part of the needle holder.
FIG. 3 shows a perspective view of that which is shown in FIG. 2.

In FIGS. 2-3 we can see that the tip of the harpoon-shaped member (11) passes through the neck of the inner part of the needle (7) when the piston is pushed with sufficient pressure until a "click" is heard showing that the two parts have locked together. This pressure allows the tip of the harpoon shaped member (11) to reach part (7) due to the fact that the material of the piston (12) is elastic and thus permits a force compression which enables it to reach the rear part of the needle.

Once the needle has caught onto the plunger it is simply a matter of extracting the aforementioned needle by an operation identical to a suction process, that is to say, pulling the plunger until the lugs (14) of the "Ω"—shaped part lock into the openings (10) located in the upper part of the cylinder. This can be seen in FIGS. 4-5.

In FIG. 10, as a result of gentle pressure on the plunger while lugs (14) are received within openings (10) the crosspieces (15) snap off, allowing the piston to travel to the end of its reach, leaving the needle fixed to the core of the piston locked into the upper part of the syringe, with no reasonable possibility of extraction. This is represented in FIGS. 6-7 where we can clearly see the gap which is maintained between the body of the piston (12) and the holder locked onto the needle (1).

Figure 11:
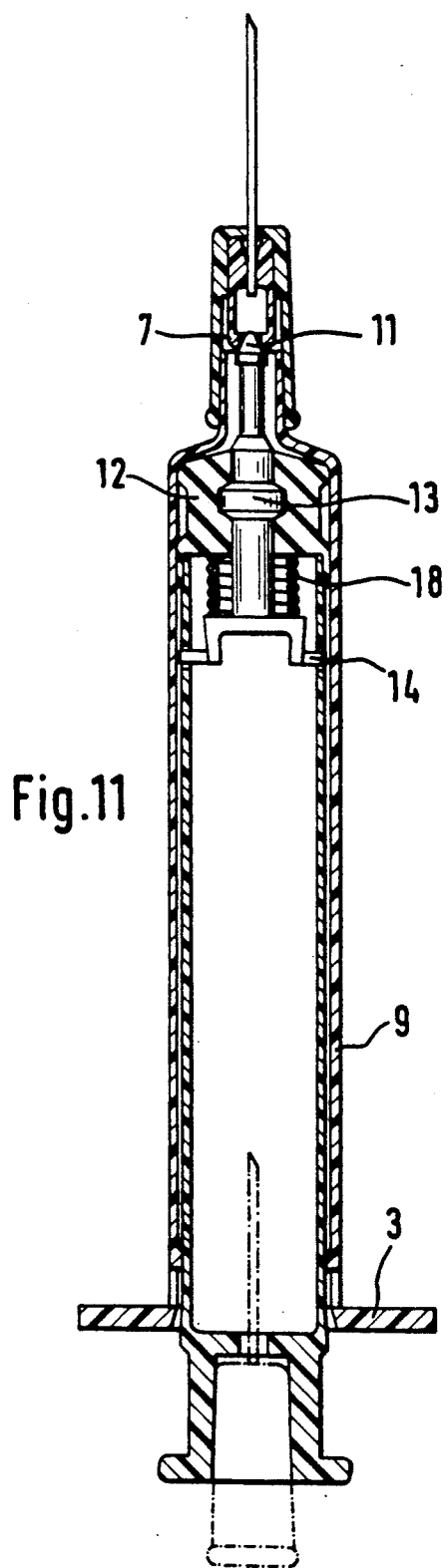
FIG. 11 shows in cross-section an alternate embodiment of the present invention.

FIG. 11 shows a possible version of a syringe with automatic extraction of the needle in which the only difference from what has been explained above consists in its being permanently fitted with a spring (18) between the elastic body of the piston (12) and the "Ω"-shaped part (14). The operation of this version is identical but it is based on the strength of the spring. In this case, the lugs at the ends of the "Ω" would break when the plunger is pressed and the tip enters part (7) of the needle as a result of the stress on the material. Once the crosspieces which prevent the spring from releasing its pressure are broken, the inner part of the plunger is released, extracting the needle in the same was as shown in the foregoing Figures.

Having explained the characteristics of the present invention we specify the protection of the same as follows.

We claim:

1. A syringe, comprising:
   a casing having a forward and rearward end and openings formed in the rearward end;
   a plunger slidable within said casing and having a forward and rearward end, the rearward end of said plunger extending outside of the rearward end of said casing, said plunger including a main body and a piston formed at the forward end of said main body;
   attachment means for attaching said plunger with a needle, said attachment means being connected to said piston and including a first member extending forwardly and out away from said piston and a second member extending rearwardly of said piston, said second member including outwardly biased locking lugs adapted to extend through apertures formed in the main body of said plunger; and
   said outwardly biased lugs being dimensioned and arranged such that, when said plunger is retracted to the rearward end of said casing, said outwardly biased lugs are received in locking fashion within said openings formed in said casing.

2. A syringe as recited in claim 1 further comprising a needle assembly which includes an inner part, an outer part, and a needle, said needle being secured at one end to said inner part, said inner part having a cavity formed therein, and said inner part being positioned within a hollow formed in said outer part, said outer part including means for attachment with the forward end of said casing, the cavity formed in said inner part being adapted to receive, in locking fashion, the first member of said attachment means, and said inner part being retained within said outer part in a manner which enables said inner part to be withdrawn away from said outer part following movement of said attachment means towards the rear end of said casing.

3. A syringe as recited in claim 2 wherein said piston is formed of elastic material and said attachment means includes a central core which extends through said piston and is positioned between said first member and said second member, and said central core being releasably retained within said elastic piston such that, when said outwardly biased locking lugs are received within the opening in said casing, an amount of forward pressure on said plunger results in said core sliding out away from said piston.

4. A syringe as recited in claim 3 wherein said apertures are in the form of elongated channels with each of said channels extending from the forward end of said plunger to the rearward end of said plunger, and said plunger including crosspieces which extend across said channels so as to define slots through which said locking lugs extend, and said slots being dimensioned so as to limit the freedom of movement of said locking lugs in a forward to rearward direction within said channels.

5. A syringe as recited in claim 4 wherein said crosspieces are relatively thin such that said crosspieces snap off following a forward thrust of said plunger with said locking lugs received within the openings in said casing.

6. A syringe as recited in claim 1 wherein said piston is formed of elastic material and said needle attachment means includes a central core which extends through said piston and is positioned between said first member and said second member, and said central core being releasably retained within said elastic piston such that, when said outwardly biased locking lugs are received within the opening in said casing, an amount of forward pressure on said lunger results in said core sliding out away from said piston.

7. A syringe as recited in claim 1 wherein said apertures are in the form of elongated channels with each of said channels extending from the forward end of said plunger to the rearward end of said lunger and said plunger including crosspieces which extend across said channels so as to define slots through which said locking lugs extend, and said slots being dimensioned so as to limit the freedom of movement of said locking lugs in a forward to rearward direction within said channels.

8. A syringe as recited in claim 1 wherein said first member is harpoon-shaped.

9. A syringe as recited in claim 8 wherein said harpoon-shaped first member includes a cone shaped tip.

10. A syringe as recited in claim 1 wherein said second member is "Ω"-shaped.

11. A syringe as recited in claim 1 wherein said piston is formed of elastic material and said attachment means includes a central core member extending within said piston, said central core member including a bulbous ring shaped member received within a complimentary recess in said piston.

12. A syringe as recited in claim 2 wherein said inner part features an inwardly extending lip at one end partially defining said cavity.

13. A syringe as recited in claim 2 wherein said first member is harpoon-shaped and includes a cone shaped tip, and said inner part is formed of an elastic material which deflects upon insertion of said cone shaped tip.

14. A syringe as recited in claim 2 wherein said first member is harpoon-shaped and includes a cone shaped tip, and said inner part includes a plurality of longitudinal channels such that said inner part deflects upon insertion of said cone shaped tip.

15. A syringe as recited in claim 2 wherein said outer part is essentially in the form of a cylinder, a forward part of which has a unitary piece and includes a rearward part having means double rim, both interior and exterior, for attaching to the forward end of the syringe casing.

16. A syringe as recited in claim 1 further comprising a spring positioned between said piston and said second member, and said apertures being in the form of elongated channels; and crosspieces extending across said channels so as to form slots within said channel within which said lug members are retained, said crosspieces acting to maintain said spring in a compressed state until sufficient forward pressure on said plunger results in the shearing of said crosspieces and the release of said spring.

17. A method of using a syringe, comprising:

forcing a plunger forward within a syringe casing with said plunger having needle attachment means extending forwardly therefrom;

further forcing said plunger forward within said casing until said needle attachment means is received in locking fashion within a cavity formed in an inner part of a needle assembly, said inner part being secured to one end of a needle;

drawing said plunger with attached needle rearwardly until outwardly biased locking members, extending to the rear of said piston and through apertures formed in said plunger, are lockingly received within openings formed at the rear of said casing.

18. The method as recited in claim 14 further comprising:

applying forward pressure to said plunger while said locking lugs are received within the openings formed at the rear of said casing until crosspieces extending across said channels snap off and said needle attachment means slips out from its releasable engagement with a piston forming part of said plunger.

19. The method as recited in claim 15 further applying forward pressure to said plunger so as to position the forward end of said plunger in contact with the forward end of said casing.

20. A method of using a syringe, comprising: forcing a plunger forward within a syringe casing with said plunger having a piston with needle attachment means extending through said piston and said needle attachment means having both a first member extending forwardly of said piston and a second member extending rearwardly away from said piston, said syringe further comprising a spring positioned between said second member and said piston;

further forcing said plunger forward within said casing until said first member is releasably locked within an inner part of a needle assembly; and still further forcing said plunger forward until crosspieces, which limit forward to rearward movement of said second member, shear off so as to allow said spring to force said needle attachment means with attached needle rearwardly until outwardly biased locking lugs forming part of said second member are received within openings formed at the rearward end of said casing.

* * * * *

UNITED STATES PATENT AND TRADEMARK OFFICE
CERTIFICATE OF CORRECTION

PATENT NO. : 5,019,043
DATED : May 28, 1991
INVENTOR(S) : Vicente M. Segui Pastor, Amando Galiana Sabater, and Enrique Segui Pastor It is certified that error appears in the above-identified patent and that said Letters Patent is hereby corrected as shown below:

Column 5;
In claim 18, in line 1, please replace "14" with --17--.
Column 6;
In claim 19, in line 1, please replace "15" with --18--.

Signed and Sealed this

Twenty-ninth Day of September, 1992

Attest:

DOUGLAS B. COMER

Attesting Officer

Acting Commissioner of Patents and Trademarks